(12) United States Patent
Gupta et al.

(10) Patent No.: US 9,097,583 B2
(45) Date of Patent: Aug. 4, 2015

(54) LONG-PATH INFRARED SPECTROMETER

(71) Applicant: Los Gatos Research, Mountain View, CA (US)

(72) Inventors: Manish Gupta, Mountain View, CA (US); J. Brian Leen, Sunnyvale, CA (US); Douglas S. Baer, Menlo Park, CA (US)

(73) Assignee: Los Gatos Research, Mountain View, CA (US)

( * ) Notice: Subject to any disclaimer, the term of this patent is extended or adjusted under 35 U.S.C. 154(b) by 0 days.

(21) Appl. No.: 13/899,358

(22) Filed: May 21, 2013

(65) Prior Publication Data

US 2014/0319352 A1    Oct. 30, 2014

Related U.S. Application Data

(60) Provisional application No. 61/650,311, filed on May 22, 2012.

(51) Int. Cl.
| | |
|---|---|
| *G01N 21/27* | (2006.01) |
| *G01N 21/59* | (2006.01) |
| *G01J 3/42* | (2006.01) |
| *G01N 21/3504* | (2014.01) |
| *G01N 21/39* | (2006.01) |

(52) U.S. Cl.
CPC ............... *G01J 3/42* (2013.01); *G01N 21/3504* (2013.01); *G01N 21/39* (2013.01)

(58) Field of Classification Search
CPC .... G01J 3/42; G01N 21/3504; G01N 21/3539
USPC ................. 250/338.1, 338.5, 339.07, 339.12, 250/339.13, 343
See application file for complete search history.

(56) References Cited

U.S. PATENT DOCUMENTS

| | | | |
|---|---|---|---|
| 5,815,277 | A | 9/1998 | Zare et al. |
| 6,795,190 | B1 | 9/2004 | Paul et al. |
| 7,468,797 | B1 | 12/2008 | O'Keefe et al. |
| 7,994,479 | B2 | 8/2011 | Wiedmann |

(Continued)

OTHER PUBLICATIONS

A. O'Keefe et al., "Cavity Ring-Down Optical Spectrometer for Absorption Measurements Using Pulsed Laser Sources", Review of Scientific Instruments, 59, 1988, 2544.
A. O'Keefe, "Integrated Cavity Output Analysis of Ultra-Weak Absorption", Chemical Physics Letters, 293, 1998, 331.

(Continued)

*Primary Examiner* — Mark R Gaworecki
(74) *Attorney, Agent, or Firm* — Thomas Schneck; Mark Protsik

(57) ABSTRACT

A tunable mid-infrared laser operated in a pulsed mode is coupled off-axis into a high-finesse optical cavity to produce a long-path spectrometer. The cavity receives a gas sample. Laser pulses may be wavelength-scanned by stepping an external grating, allowing the grating to mechanically settle, then measuring the ring-down with a set of laser pulses, before moving on the next wavelength. A detector receiving infrared light exiting the cavity supplies a cavity ring-down trace representative of sample absorption of the infrared pulses. A processor determines an absolute absorption spectrum of the gas sample from the ring-down trace and analyzes sample gas composition and trace concentration from that spectrum. The absorption baseline is highly reproducible and stable, improving the accuracy of multivariate fits, and the spectral resolution can be better than 0.001 cm$^{-1}$ (contingent upon the laser source), allowing for high-resolution measurements of sharp absorption features.

20 Claims, 1 Drawing Sheet

(56) References Cited

U.S. PATENT DOCUMENTS

| | | |
|---|---|---|
| 8,063,373 B2 | 11/2011 | Miller |
| 2009/0180119 A1* | 7/2009 | Reeve et al. .............. 356/437 |
| 2010/0051813 A1 | 3/2010 | Xiao et al. |
| 2011/0270113 A1 | 11/2011 | Heyne et al. |
| 2011/0295140 A1 | 12/2011 | Zaidi et al. |

OTHER PUBLICATIONS

D.S. Bear et al., "Sensitive Absorption Measurements in the Near-Infrared Region Using Off-Axis Integrated-cavity-output Spectroscopy", Applied Physics B, 75, 2002, 261.

K. Lehmann et al., Optimal Signal Processing in Cavity Ring-Down Spectroscopy, Frontiers of Molecular Spectroscopy, Jaan Laane, editor (Elsevier 2009), pp. 623-657.

\* cited by examiner

LONG-PATH INFRARED SPECTROMETER

CROSS-REFERENCE TO RELATED APPLICATION

This application claims priority under 35 U.S.C. 119(e) from prior U.S. provisional application No. 61/650,311, filed May 22, 2012.

STATEMENT REGARDING FEDERALLY-SPONSORED RESEARCH AND DEVELOPMENT

This invention was made with government support under contract number W911SR-09-C-0060 awarded by the Department of Defense. The government has certain rights in the invention.

TECHNICAL FIELD

The present invention relates to absorption spectroscopy and spectrometers operating in the mid-infrared spectrum.

BACKGROUND ART

Mid-infrared spectroscopy is used for a wide array of applications including environmental sensing, trace detection of hazardous materials, pharmaceutical manufacturing, and medical diagnostics. The most common mid-infrared spectroscopy is Fourier Transform Infrared (FTIR) spectroscopy. In FTIR spectroscopy, mid-infrared light from a broadband source (lamp, glow bar, etc.) is passed through a sample and onto an interferometer. The interferometer is adjusted and the Fourier transform of the transmitted light signal is used to determine the absorption spectrum. For example, the sample may contain some quantity of one or more volatile organic compounds (VOCs) that need to be detected, identified and/or measured. For trace detection applications, the sample path length is sometimes extended (e.g. long open path measurements) to provide larger absorption signals. However, the optical path length is typically limited in FTIR spectroscopy to 10-100 meters. Additionally, the absorption baseline is usually neither stable nor smooth (thereby limiting the accuracy with which you can determine small optical absorptions), and the spectral resolution if often limited to approximately $1.0\ cm^{-1}$.

It is known that a high-finesse optical cavity can be used to provide a very long effective optical path length (1-10 km, typical). See, for example: A. O'Keefe and D. A. G. Deacon, "Cavity ring-down optical spectrometer for absorption measurements using pulsed laser sources", *Review of Scientific Instruments* 59 (1988) 2544; A. O'Keefe, "Integrated cavity output analysis of ultra-weak absorption", *Chemical Physics Letters* 293 (1998) 331; D. S. Baer, J. B. Paul, M. Gupta, A. O'Keefe, "Sensitive absorption measurements in the near-infrared region using off-axis integrated-cavity-output spectroscopy", *Applied Physics B* 75 (2002) 261; and U.S. Pat. No. 6,795,190, "Absorption spectroscopy instrument with off-axis light insertion into cavity".

Recent developments in quantum cascade laser (QCL) technology, optical parametric oscillators (OPOs), and difference-frequency generation (DFG) sources have resulted in widely-tunable lasers in the mid-infrared with central wavelengths spanning from 3-11 microns. Quantum cascade lasers are generally made for operation in continuous mode. Additionally, while they are tunable they are also external cavity devices with an external grating that needs to mechanically settle after tuning to a specified wavelength before stable use at that new wavelength becomes possible, particularly if accurate measurements are to be made.

SUMMARY DISCLOSURE

In the present invention, we couple these recently-developed, widely-tunable lasers with high-finesse optical cavities (e.g., cavity ring-down spectroscopy) to produce a long-path, mid-infrared spectrometer. The resulting spectrometer has several advantages over existing technology, including 1) a very long effective optical path length (>1 km, typical) for trace detection, 2) the absorption baseline (e.g. optical loss as a function of wavelength) is highly reproducible and stable, improving the accuracy of multivariate fits, and 3) the spectral resolution can be better than $0.001\ cm^{-1}$ (contingent upon the laser source), allowing for high-resolution measurements of sharp absorption features.

To achieve these results in cavity ring down systems using quantum cascade lasers, we operate such lasers in a pulsed mode rather than in the continuous mode for which they are made. Further, although it is necessarily more time consuming, in order to create a full absorption spectrum by scanning a quantum cascade laser over its operational wavelength range, rather than scanning the wavelengths continuously, we step the external grating, allow it to mechanically settle, then measure the ring down with a set of laser pulses, before moving on to the next wavelength. This repeated stepping, settling and pulsing provides more stable and accurate measurement results.

DETAILED DESCRIPTION

The term "mid-infrared" is used throughout this application. The definition is still somewhat unsettled, with the boundaries between near, mid and far infrared varying in different scientific and technological fields. Generally, the near-infrared/mid-infrared boundary in various definitions occurs anywhere from 1.4 to 3.0 μm, while the mid-infrared/far-infrared boundary varies from 15 μm to as long as 40 or 50 μm. In the present application, we adopt a range for mid-infrared that is generally employed in the field of spectroscopy, namely from 2.5 μm to 25 μm ($4000\ cm^{-1}$ to $400\ cm^{-1}$). In practice, the wavelengths employed by instruments in accord with the present invention will be limited solely by the availability of suitable laser sources, optical cavity reflectors, and infrared detectors and by the usefulness of the sample absorption wavelengths in detecting, measuring and analyzing the sample composition and concentration.

Figure 1:
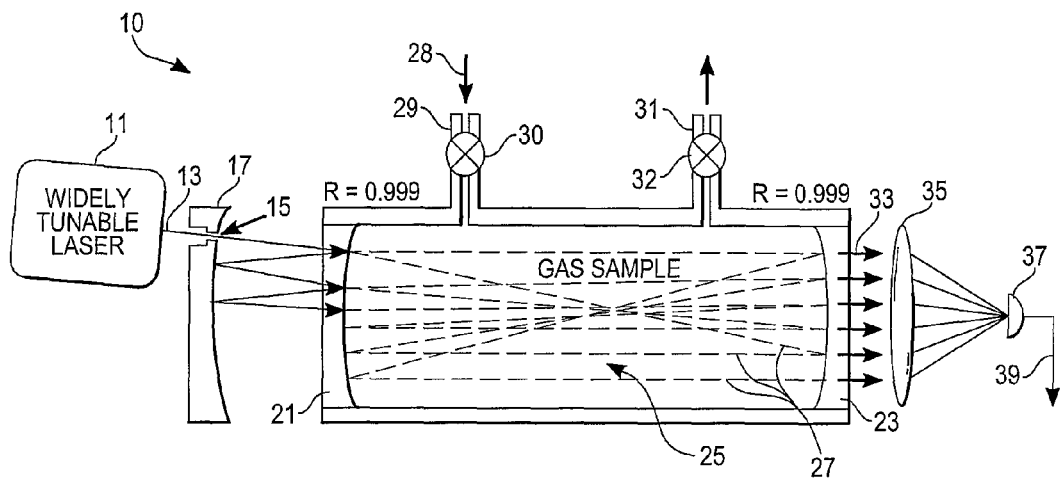
FIG. 1 illustrates one possible embodiment of the invention, which uses a widely-tunable, external-cavity quantum cascade laser coupled to a high-finesse optical cavity in an off-axis fashion. The laser is pulsed and the resulting off-axis cavity ring-down traces are analyzed to determine the optical loss in the cavity as a function of laser wavelength.

An embodiment in accord with the present invention is shown in FIG. 1. For the tunable mid-infrared laser source 11 we use a commercial off-the-shelf laser, such as an external-cavity quantum cascade laser. The mid-infrared laser light 13 is coupled into a high-finesse optical cavity, defined by mirrors 21 and 23 bounding a sample cell 25, to develop a long-path mid-infrared spectrometer 10. The laser light 27 may be injected into the cavity in an off-axis manner, which is robust and easy to align. Alternatively, if the laser light is injected on-axis into the cavity, a higher signal-to-noise ratio can be achieved, allowing use of a smaller detector. Light reflected off an optional front re-injection mirror 17 (with a small opening 15 for initial passage of the laser light 13) may be reinserted thereby into the cavity (as described in U.S. Pat. No. 7,468,797, "Absorption spectroscopy instrument with increased optical cavity power without resonant frequency build-up") to increase the effective intra-cavity laser power. Alternative cavity geometries, such as (a) a ring cavity, (b) a total internal reflector cavity, or (c) multiple (3+) mirror cavity, may be used in place of the usual two-mirror linear cavity. The high-reflectivity (e.g. R=0.999) cavity mirrors 21 and 23 may be planar or curved. What matters most is that the cavity has a high finesse to increase the effective path length (>1 km, typical) of the inserted laser light 27 through the sample cell 25.

Sample gas 28 is provided to the cavity through a sample inlet 29 and outlet 31 with corresponding flow valves 30 and 32 and pump(s) (not shown). The sample 28 can be preconditioned prior to introduction into the cell 25 using any of a variety of available techniques, for example, using a Nafion dryer to remove water vapor. Likewise, the sample may be speciated, using either a gas chromatograph or a thermal desorption unit to separate compounds prior to measurement and spectroscopy. Note that the cell 25, mirrors 21 and 23 and inlet plumbing 29 and 30 can be heated to 110° C. (or higher) when needed to enable measurement of large volatile organic compounds or other low vapor pressure molecules. Additionally, in order to increase molecular absorption, the cell pressure can be increased. The detection limit increases linearly with pressure.

A detector 37 is positioned to receive and detect infrared light 33 exiting the cavity so as to supply a cavity ring-down trace 39 that is representative of sample absorption by the infrared laser pulses. Choice of infrared detector (e.g., HgCdTe, InSb, PbSe, PtSi) will depend upon the mid-infrared wavelength range of interest. Infrared detectors are operated at cryogenic temperatures in order to substantially reduce thermal noise in the detection, being cooled, e.g. with a supply of liquid nitrogen ($LN_2$), a Sterling engine, or thermoelectric (TE) cooler. While FIG. 1 shows collection 35 of light 33 exiting through only one side of the cavity (through cavity mirror 23), light can be collected through both front and back mirrors (or multiple mirrors in ring cavity and other configurations) in order to increase the incident light flux on the detector.

The spectrometer may be operated in a cavity ring-down mode. The laser 11 is operated in pulsed-mode and slowly scanned in wavelength over its operational range (e.g. 9-11 microns). Each pulse results in a cavity ring-down trace 39 that is analyzed to determine the optical loss in the cavity as a function of laser wavelength. Laser wavelength stability is established by examining intensity time traces on the detector and adjusting the step delay such that transients are fully damped before data collection begins. Thus, after execution of each step command for which the laser output is stepped to a new wavelength, data collection is delayed until the requisite time has passed for laser stabilization, as determined by a PC-based clock. Stability of the cavity ring-down traces is maximized by choosing an alignment that optimizes the ring-down signal-to-noise ratio (defined as fit amplitude divided by fit residual max-min) rather than ring-down amplitude. Detector-amplifier nonlinearities are minimized by a PID feedback loop on the ring-down fit offset, which keeps the amplifier gain stage input offset at or near zero to eliminate changes in the impedance matching between the detector and the amplifier. This feature greatly improves the instrument's signal-to-noise ratio. Ring-down collection is performed with a data acquisition card having sufficient sample rate to collect a minimum of 10 to 20 points per time constant. If desired, the laser can be actively swept while measuring ring-down traces in order to decrease analyzer response time.

A processor (not shown) that receives the ring-down cavity trace 39 from the detector 37 is configured to determine an absolute absorption spectrum of the gas sample 28 and to analyze sample gas composition and trace concentration of identified compounds from that spectrum. Accordingly, the cavity loss versus wavelength represented by the ring-down is converted to an absolute absorption spectrum that can be analyzed to determine the gas composition. In particular, digitized ring-down traces are fit using non-linear least squares to a single exponential: $y=y_0+A^*e^{-t/\tau}$. This method of extracting the ring-down time constant $\tau$ has been shown to be optimal, particularly for low signal-to-noise ratios. Cf. Kevin K. Lehmann and Haifeng Huang, "Optimal signal processing in cavity ring-down spectroscopy", *Frontiers of Molecular Spectroscopy*, Jaan Laane, editor (Elsevier 2009), pp. 623-657. Absorption from target analytes is calculated by subtracting background cavity loss [$=1/(c \cdot \tau)$] from the measured loss. Background cavity loss can be measured periodically by filling the cavity with VOC-free air. This periodic loss calibration eliminates errors due to environmentally-induced drift (especially temperature).

While FIG. 1 shows only a single cavity, the technology can be also be used with multiple cavities simultaneously working at different sets of wavelengths in parallel. Likewise, the different cavities could work at the same wavelength but upon different portions of a speciated sample, using the same or a different laser to supply the various cavities.

Figure 2:
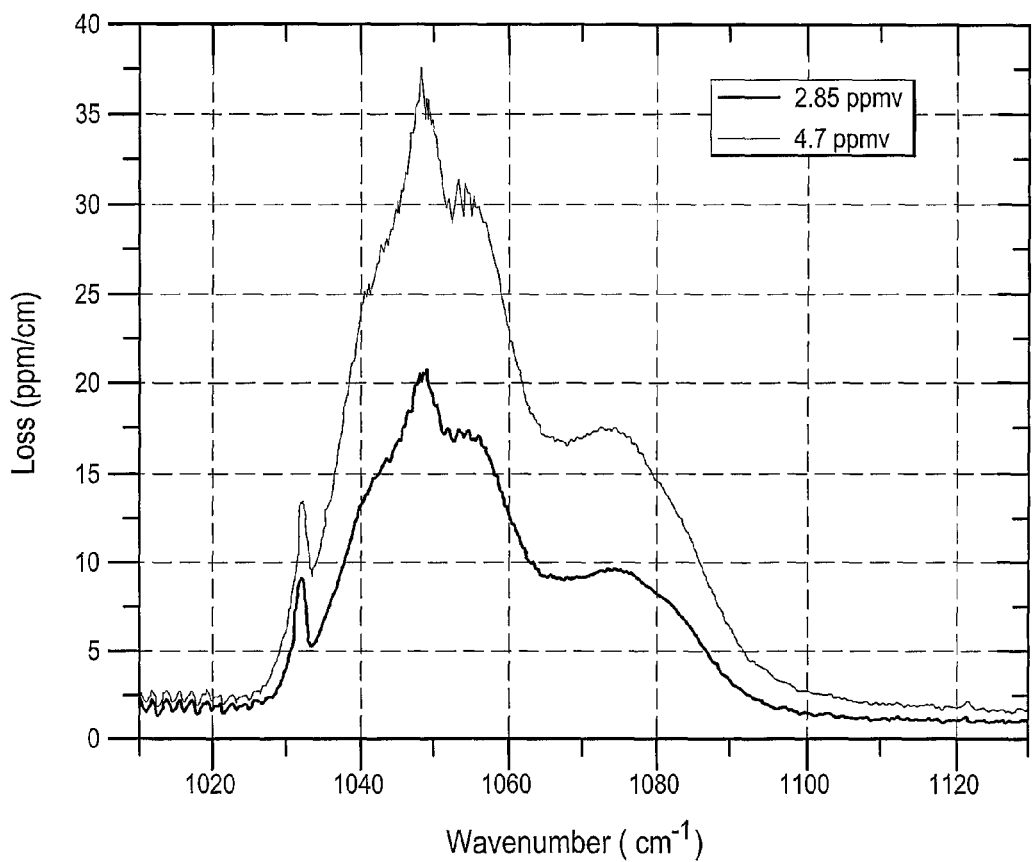
FIG. 2 shows an example of the measured absorption spectrum using the present invention. The depicted spectrum in this example is of dimethyl methylphosphonate (DMMP).

An example spectrum of DMMP (dimethyl methylphosphonate, a sarin simulant) that was measured using the apparatus depicted in FIG. 1 is shown in FIG. 2. Note that the device accurately quantifies trace levels of DMMP, is highly reproducible, and can readily discern the fine structure on the absorption features.

What is claimed is:

1. A mid-infrared spectrometer, comprising:
   a wavelength-tunable pulsed-mode infrared laser;
   an optical cavity having a finesse defined by at least 0.999 reflectivity mirrors, the cavity bounds a sample cell with an inlet and outlet for receiving a gas sample therein, with wavelength-scanned infrared pulses from the laser being coupled into the optical cavity, the pulses having an effective optical path length in the cavity of at least 1 km;
   a detector positioned to receive and detect infrared light exiting the cavity so as to supply a cavity ring-down trace representative of sample absorption by the infrared pulses; and
   a processor coupled to receive the ring-down trace from the detector, the processor configured to determine an absolute absorption spectrum of the gas sample and analyze sample gas composition and trace concentration from that spectrum.

2. The spectrometer as in claim 1, wherein the infrared pulses from the laser are coupled off-axis into the optical cavity.

3. The spectrometer as in claim 1, wherein the infrared pulses from the laser are coupled on-axis into the optical cavity.

4. The spectrometer as in claim 1, wherein the optical cavity is a two-mirror linear cavity.

5. The spectrometer as in claim 1, wherein the optical cavity is selected from any of a ring cavity, a total internal reflection cavity, and a three or more mirror cavity configuration.

6. The spectrometer as in claim 1, wherein the sample cell, inlet and cavity mirrors are heated to at least 110° C.

7. The spectrometer as in claim 1, wherein the gas sample received in the sample cell exceeds ambient pressure.

8. The spectrometer as in claim 1, wherein the detector is cryogenically cooled by any of supply of liquid nitrogen, a Sterling engine, and thermo-electric cooler.

9. A method of operating a mid-infrared spectrometer for absorption spectroscopy of a gas sample, comprising:
supplying a gas sample to a sample cell bounded by an optical cavity, the cavity having a finesse defined by at least 0.999 reflectivity mirrors;
injecting pulses of infrared light from a wavelength-tunable infrared laser into the optical cavity, the injected pulses having an effective optical path length in the cavity of at least 1 km, the injected pulses being subject to sample absorption by gas sample in the sample cell;
collecting and detecting infrared light exiting the cavity by a detector so as to supply a cavity ring-down trace representative of the sample absorption; and
a processing the ring-down trace from the detector so as to determine an absolute absorption spectrum of the gas sample.

10. The method as in claim 9, further comprising analyzing sample gas composition and trace concentration from the absolute absorption spectrum.

11. The method as in claim 9, wherein the infrared laser is stepwise tuned over a range of wavelengths, data collection of the ring-down trace being delayed after stepping until transients are adequately damped.

12. The method as in claim 9, wherein the gas sample is preconditioned prior to being supplied to the sample cell.

13. The method as in claim 9, wherein the gas sample is speciated by a selected compound separation technique prior to being supplied to the sample cell.

14. The method as in claim 9, wherein the gas sample is heated to at least 110° C. as it is supplied to the sample cell.

15. The method as in claim 9, wherein the gas sample received in the sample cell exceeds ambient pressure.

16. The method as in claim 9, wherein the infrared pulses from the laser are coupled off-axis into the optical cavity.

17. The method as in claim 9, wherein the infrared pulses from the laser are coupled on-axis into the optical cavity.

18. The method as in claim 9, wherein the optical cavity is a two-mirror linear cavity.

19. The method as in claim 9, wherein the optical cavity is selected from any of a ring cavity, a total internal reflection cavity, and a three or more mirror cavity configuration.

20. The method as in claim 9, wherein the detector is cryogenically cooled by any of supply of liquid nitrogen, a Sterling engine, and thermo-electric cooler.

* * * * *